(12) United States Patent
Shen et al.

(10) Patent No.: US 11,166,644 B2
(45) Date of Patent: Nov. 9, 2021

(54) MODULE FOR DETECTING ELECTRICAL SIGNALS FROM BODY SKIN

(71) Applicant: TAIWAN TEXTILE RESEARCH INSTITUTE, New Taipei (TW)

(72) Inventors: Chien-Lung Shen, New Taipei (TW); Chien-Fa Tang, New Taipei (TW); Kun-Chuan Tsai, New Taipei (TW); Fen-Ling Chen, New Taipei (TW); Ya-Chi Ko, New Taipei (TW)

(73) Assignee: TAIWAN TEXTILE RESEARCH INSTITUTE, New Taipei (TW)

( * ) Notice: Subject to any disclaimer, the term of this patent is extended or adjusted under 35 U.S.C. 154(b) by 328 days.

(21) Appl. No.: 16/152,619

(22) Filed: Oct. 5, 2018

(65) Prior Publication Data

US 2019/0029558 A1 Jan. 31, 2019

Related U.S. Application Data

(62) Division of application No. 15/097,430, filed on Apr. 13, 2016, now abandoned.

(30) Foreign Application Priority Data

May 6, 2015 (TW) .................................. 104114463
May 7, 2015 (TW) .................................. 104114596

(51) Int. Cl.
*D02G 3/44* (2006.01)
*A61B 5/0531* (2021.01)
(Continued)

(52) U.S. Cl.
CPC ............ *A61B 5/0531* (2013.01); *A61B 5/282* (2021.01); *A61B 5/291* (2021.01); *A61B 5/6805* (2013.01);
(Continued)

(58) Field of Classification Search
CPC ....... A61B 5/0531; A61B 5/291; A61B 5/282; A61B 5/6805; A61B 5/6831; D02G 3/441; D03D 11/00; D03D 27/04
See application file for complete search history.

(56) References Cited

U.S. PATENT DOCUMENTS 4,850,942 A 7/1989 Dalferth
8,560,044 B2 10/2013 Kurzweil et al.
(Continued)

FOREIGN PATENT DOCUMENTS

CN 202654120 U 1/2013
CN 203168043 U 9/2013
(Continued)

OTHER PUBLICATIONS

H.-Y. Song et al, "Textile Electrodes of Jacquard Woven Fabrics for Biosignal Measurement", Journal of the Textile Institute, vol. 101, No. 8, Aug. 1, 2010, pp. 758-770, XP055174668.
(Continued)

*Primary Examiner* — Daniel L Cerioni
(74) *Attorney, Agent, or Firm* — McClure, Qualey & Rodack, LLP

(57) ABSTRACT

A stereoscopic conductive fabric includes a basement yarn layer, a conductive yarn, and a support yarn. The basement yarn layer includes plural warp yarns arranged coursewise and parallel to each other and plural course yarns arranged warpwise and parallel to each other. The course yarns are interwoven with the warp yarns to form the basement yarn layer. The conductive yarn is arranged coursewise and interwoven with the course yarns in a skip manner to form plural conductive structures protruding from a surface of the basement yarn layer. The support yarn is arranged coursewise and interwoven with the course yarns in a skip manner to form plural pressing structures protruding from another surface of the basement yarn layer. A module for detecting (Continued)

electrical signals from body skin applying the stereoscopic conductive fabric is also disclosed.

15 Claims, 9 Drawing Sheets

(51) Int. Cl.
    *D03D 1/00*     (2006.01)
    *A61B 5/00*     (2006.01)
    *D03D 11/00*     (2006.01)
    *D03D 27/04*     (2006.01)
    *A61B 5/282*     (2021.01)
    *A61B 5/291*     (2021.01)
    *A61B 5/25*     (2021.01)

(52) U.S. Cl.
    CPC ........... *A61B 5/6831* (2013.01); *D02G 3/441* (2013.01); *D03D 1/0088* (2013.01); *D03D 11/00* (2013.01); *D03D 27/04* (2013.01); *A61B 5/25* (2021.01); *A61B 2562/125* (2013.01); *A61B 2562/18* (2013.01); *D10B 2401/16* (2013.01); *D10B 2401/18* (2013.01); *D10B 2509/00* (2013.01)

(56) References Cited

U.S. PATENT DOCUMENTS

| | | |
|---|---|---|
| 2009/0277528 A1 | 11/2009 | Shen et al. |
| 2013/0172722 A1 | 7/2013 | Ninane et al. |
| 2014/0012145 A1 | 1/2014 | Kurzweil et al. |
| 2014/0039292 A1 | 2/2014 | Su et al. |
| 2014/0220845 A1* | 8/2014 | Elder ................. B32B 27/12 442/198 |
| 2014/0242868 A1 | 8/2014 | Huang et al. |
| 2014/0243639 A1 | 8/2014 | Huang et al. |
| 2014/0343392 A1 | 11/2014 | Yang |
| 2016/0324439 A1 | 11/2016 | Shen et al. |

FOREIGN PATENT DOCUMENTS

| | | |
|---|---|---|
| DE | 202012102025 U1 | 8/2012 |
| DE | 202012102353 U1 | 8/2012 |
| DE | 202013100455 U1 | 5/2013 |
| EP | 0269557 A1 | 6/1988 |
| EP | 2582290 B1 | 5/2014 |
| EP | 2770092 A1 | 8/2014 |
| JP | 3177243 U | 7/2012 |
| JP | 3178230 U | 9/2012 |
| TW | M435255 U | 8/2012 |
| TW | M440760 U | 11/2012 |
| TW | M457026 U | 7/2013 |
| WO | 2013075388 A1 | 5/2013 |

OTHER PUBLICATIONS

"AGY introduces 99 GPA tensile modulus glass fibre," Materials Today, 2012.
"Modulus of Elasticity—Young Modulus for some common Materials," Engineering Toolbox, 2014.

* cited by examiner

MODULE FOR DETECTING ELECTRICAL SIGNALS FROM BODY SKIN

RELATED APPLICATIONS

This application is a Divisional Application of the U.S. application Ser. No. 15/097,430, filed Apr. 13, 2016, which claims priority to Taiwan Application Serial Number 104114463, filed May 6, 2015, and also claims priority to Taiwan Application Serial Number 104114596, filed May 7, 2015, all of which are herein incorporated by reference.

BACKGROUND

Field of Invention

The present invention relates to a stereoscopic conductive fabric and a detecting module using the same.

Description of Related Art

The prior art methods for detecting signals, such as an electrocardiogram (ECG), an eye on gambling (EOG) signal, an electroencephalogram (EEG), or an electromyogram (EMG), etc., usually utilize airtight electrode patches to be affixed to surfaces of human bodies to obtain electrical signals. The drawback is that the electrode patches adhere to skin for such a long time that the skin cannot breathe and sweat, thus easily making the subjects feel uncomfortable. As a result, the rejection of electrode patches will affect the testing quality.

In view of the above, the technology of using a conductive fabric as the electrode patch is developed. However, since the conductive fabric itself is relatively light and thin, it usually needs to cooperate with an additional elastic pad, such as a rubber material, which is adhered to the body skin so that the electrode pad made of the conductive fabric can closely touch the skin. Nevertheless, this combination of heterogeneous materials will increase the thickness of the electrode pad, thus the appearance of the electrode pad is not flat.

For the forgoing reasons, there is a need to solve the above-mentioned problem by providing a stereoscopic conductive fabric.

SUMMARY

Therefore, the present invention provides a stereoscopic conductive fabric having pressing structures to allow the stereoscopic conductive fabric to touch against the body skin.

Furthermore, the present invention also provides a module for detecting electrical signals from body skin applying the stereoscopic conductive fabric. The module is able to store excess moisture, such that the problem of conventional electrode pad is short because of sweat or is failed when the weather is too dry can be prevented.

A stereoscopic conductive fabric is provided. The stereoscopic conductive fabric comprises a basement yarn layer, a conductive yarn, and a support yarn. The basement yarn layer comprises a plurality of warp yarns arranged coursewise and parallel to each other and a plurality of course yarns arranged warpwise and parallel to each other. The course yarns are interwoven with the warp yarns to form the basement yarn layer. The conductive yarn is arranged coursewise and interwoven with the course yarns in a skip manner to form a plurality of conductive structures protruding from a surface of the base yarn layer. The support yarn is arranged coursewise and interwoven with the course yarns in a skip manner to from a plurality of pressing structures protruding from another surface of the basement yarn layer.

The invention provides a module for detecting electrical signals from body skin detachably fastened on a fabric for touching body skin. The module for detecting electrical signals from body skin comprises a hydrophobic carrier, at least one stereoscopic conductive fabric, and a conducting device. The stereoscopic conductive fabric is disposed on the hydrophobic carrier and comprises a basement yarn layer and a plurality of conductive structures and a plurality of pressing structures respectively disposed on two opposite surfaces of the basement yarn layer. The stereoscopic conductive fabric touches the hydrophobic carrier with the pressing structures and touches the body skin with the conductive structures. The conducting device is disposed on the hydrophobic carrier and electrically connected to the conductive structures to transmit electrical signals generated by the conductive structure.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE EMBODIMENTS

Figure 1:
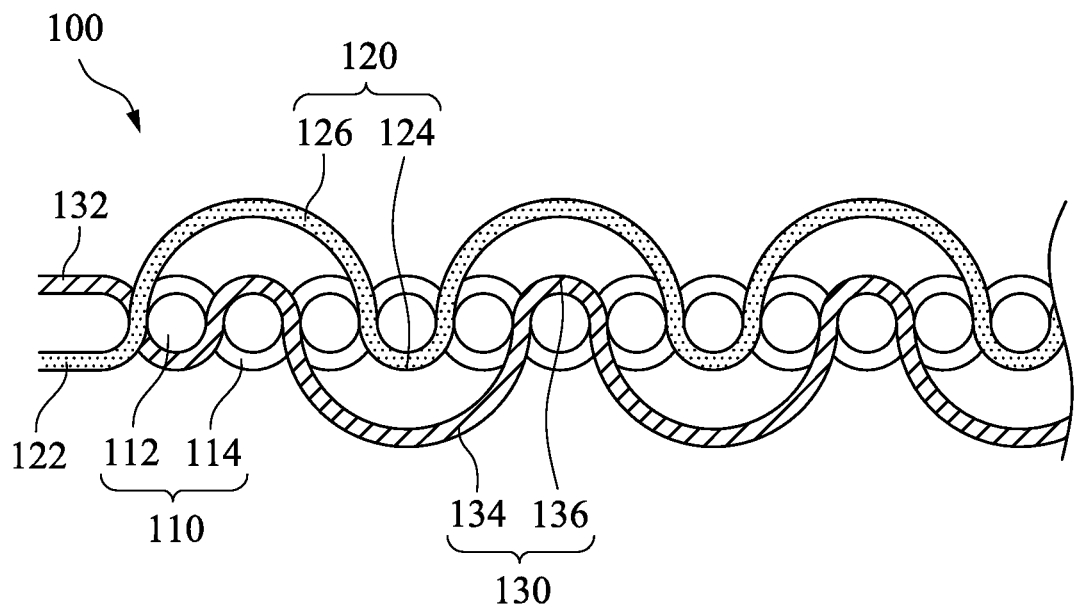
FIG. 1 is a side schematic diagram of a stereoscopic conductive fabric according to one embodiment of this invention.

Reference will now be made in detail to the present embodiments of the invention, examples of which are illustrated in the accompanying drawings. Wherever possible, the same reference numbers are used in the drawings and the description to refer to the same or like parts.

In order to allow the conductive fabric to closely touch skin and fulfill the requirements of comfort and aesthetics when being applied to a physiological sensing electrode pad, the present invention provides a stereoscopic conductive fabric. By using a special weaving method, not only does the stereoscopic conductive fabric have an electrically conductive function, but it also has good pressurized elasticity.

A description is provided with reference to FIG. 1. FIG. 1 is a side schematic diagram of a stereoscopic conductive fabric according to one embodiment of this invention. A stereoscopic conductive fabric 100 can be affixed to clothing to touch body skin of a wearer so as to perform detection. The stereoscopic conductive fabric 100 comprises a basement yarn layer 110, and conductive structures 120 and pressing structures 130 respectively protruding from two opposite surfaces of the basement yarn layer 110. The conductive structures 120 are a surface of the stereoscopic conductive fabric 100 used for touching the body skin. The pressing structures 130 are disposed on a surface of the basement yarn layer 110 opposite to the conductive structures 120 and between the clothing and the body skin to provide a supportive elastic force to the stereoscopic conductive fabric 100, so that the conductive structures 120 can closely touch the body skin.

The basement yarn layer 110 of the stereoscopic conductive fabric 100 comprises course yarns 112 arranged warpwise and parallel to each other and warp yarns 114 arranged coursewise and parallel to each other. The warp yarns 114 are interwoven with the course yarns 112 to form the basement yarn layer 110. In the present embodiment, the basement yarn layer 110 is a single-layered structure, and a material of the basement yarn layer 110 is preferably a yarn having a good water absorption property. As a result, the basement yarn layer 110 is able to provide a moisture absorption property.

The course yarns 112 and the warp yarns 114 may be a combination of conductive fibers and insulating yarns. For example, the course yarns 112 are conductive yarns and the warp yarns 114 are insulating yarns. Or, the course yarns 112 are insulating yarns and the warp yarns 114 are conductive yarns. Or, the course yarns 112 and the warp yarns 114 are both conductive yarns. Or, the course yarns 112 and the warp yarns 114 are both insulating yarns. In some embodiments, the course yarns 112 can even comprise the conductive yarns and the insulating yarns, or the warp yarns 114 can even comprise the conductive yarns and the insulating yarns.

The stereoscopic conductive fabric 100 further comprises conductive yarns 122 and support yarns 132. The conductive yarns 122 and the support yarns 132 are arranged in parallel to the warp yarns 114 and similarly interweave with the course yarns 112. In greater detail, the conductive yarns 122, the support yarns 132, and the warp yarns 114 are all arranged coursewise and parallel to one another, and the conductive yarns 122, the support yarns 132, and the warp yarns 114 can be arranged alternately. A ratio of numbers of the conductive yarns 122, the support yarns 132, and the warp yarns 114 may vary depending on various design requirements.

The conductive yarns 122 are interwoven with the course yarns 112 in a skip manner to form the conductive structures 120 protruding from a surface of the basement yarn layer 110 from the conductive yarns 122. In greater detail, the conductive structures 120 constituted by the conductive yarns 122 have wave troughs 124 hidden in the basement yarn layer 110 and wave crests 126 exposed from the basement yarn layer 110. A width of the wave crests 126 is greater than a width of the wave troughs 124, such that the wave crests 126 of the conductive yarns 122 protrude from the surface of the basement yarn layer 110 to form the conductive structures 120 protruding from the surface of the basement yarn layer 110 due to the recovery of yarns themselves after the stereoscopic conductive fabric 100 is woven.

In the present embodiment, the conductive yarns 122 are skipped at a fixed interval. For example, each of the wave crests 126 of the conductive yarns 122 may cross three course yarns 112, and each of the wave troughs 124 of the conductive yarns 122 may cross one course yarn 112. Although a ratio of the width of the wave crests 126 to the width of the wave troughs 124 is 3:1 according to the present embodiment, however in other embodiments, the ratio of the width of the wave crests 126 to the width of the wave troughs 124 may be 2:1, 4:1, 3:2, etc., as long as the width of the wave crests 126 of the conductive yarns 122 is greater than the width of the wave troughs 124 of the conductive yarns 122.

The conductive yarns 122 comprise conductive fibers. In some embodiments, the conductive yarn 122 may comprise two or more conductive fibers with different materials twisted together. In some embodiments, the conductive yarn 122 may comprise two or more conductive fibers having different electric conductivities twisted together. However, the present invention is not limited in this regard. In other embodiments, the conductive yarn 122 may be constituted by a single type of conductive yarn.

The conductive yarn 122, in addition to providing an electrically conductive function, can further be selected from fiber materials having a good water conductivity property and good elasticity. Since the conductive yarns 122 have the good water conductivity property, the conductive structures 120 are able to absorb excess water on the body skin by way of the capillary effect, and the excess water is stored in the basement yarn layer 110 contacting the conductive structures 120 and having a good water absorption property so as to avoid a short circuit between the conductive structures 120 because of excess water. Under the circumstances, the water absorption property of the basement yarn layer 110 is better than water absorption properties of the conductive yarns 122 and the support yarns 132. The conductive yarns 122 have good elasticity that allows the protruding conductive structures 120 to have a sufficient support force when being pressed.

The support yarns 132 are similarly interwoven with the course yarns 112 in a skip manner to form the pressing structures 130 protruding from another surface of the basement yarn layer 110. In greater detail, the support yarns 132 have wave crests 136 hidden in the basement yarn layer 110 and wave troughs 134 exposed from the basement yarn layer 110. A width of the wave troughs 134 is greater than a width of the wave crests 136, such that the wave troughs 134 of the support yarns 132 protrude from the another surface of the basement yarn layer 110 to form the pressing structures 130 protruding from the another surface of the basement yarn layer 110 due to the recovery of yarns themselves after the stereoscopic conductive fabric 100 is woven.

In the present embodiment, the support yarns 132 are skipped at a fixed interval. For example, each of the wave crests 136 of the support yarns 132 crosses one course yarn 112, and each of the wave troughs 134 of the support yarns 132 crosses three course yarns 112. In addition, the wave crests 136 of the support yarn 132 are preferably not aligned with the wave crests 126 of the conductive yarn 122 adjacent to the support yarn 132. Similarly, although a ratio of a width of the wave troughs 134 of the support yarns 132 to a width of the wave crests 136 of the support yarns 132 is 3:1 according to the present embodiment, however in other embodiments, the ratio of the width of the wave troughs 134 to the width of the wave crests 136 may be 2:1, 4:1, 3:2, etc., as long as the width of the wave troughs 134 of the support yarns 132 is greater than the width of the wave crests 136 of the support yarns 132.

Stiffness of the support yarns 132 is preferably greater than stiffness of the basement yarn layer 110 and the conductive yarns 122 to allow the pressing structures 130 constituted by the support yarns 132 to be less easy to deform, as compared with the conductive structures 120. When a wearer wears clothing having the stereoscopic conductive fabric 100, especially more clinging clothing, the pressing structures 130 located between the clothing and the body skin can provide a supportive elastic force so that the conductive structures 120 touch against the body skin.

Figure 2:
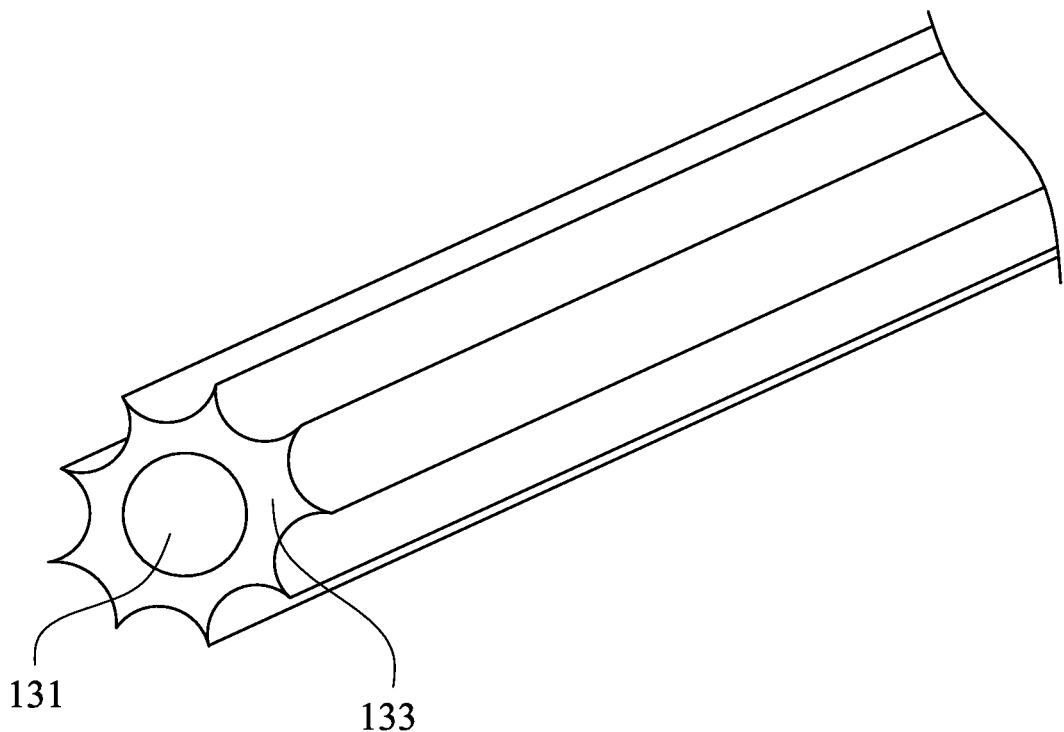
FIG. 2 is a schematic diagram of a support yarn applied to a stereoscopic conductive fabric according to one embodiment of this invention.

Not only can the support yarns 132 provide the supportive elastic force, but the support yarns 132 can also have effects of electrical conduction, moisture absorption and water conduction, etc. A detailed description is provided with reference to FIG. 2. FIG. 2 is a schematic diagram of a support yarn applied to a stereoscopic conductive fabric according to one embodiment of this invention. The support yarn 132 may be a yarn in a core-sheath structure. The support yarn 132 comprises a core layer 131 and a sheath layer 133 enclosing the core layer 131. The core layer 131 may be selected from rigid materials with greater stiffness so as to support. A material of the surrounding sheath layer 133 may be a material having conductivity, such as a conductive fiber, and/or a material having moisture absorption and water conduction properties, such as cotton or rayon, etc. In this manner, the support yarns 132 are able to have effects of support, electrical conduction, moisture absorption and water conduction at the same time.

Figure 3:
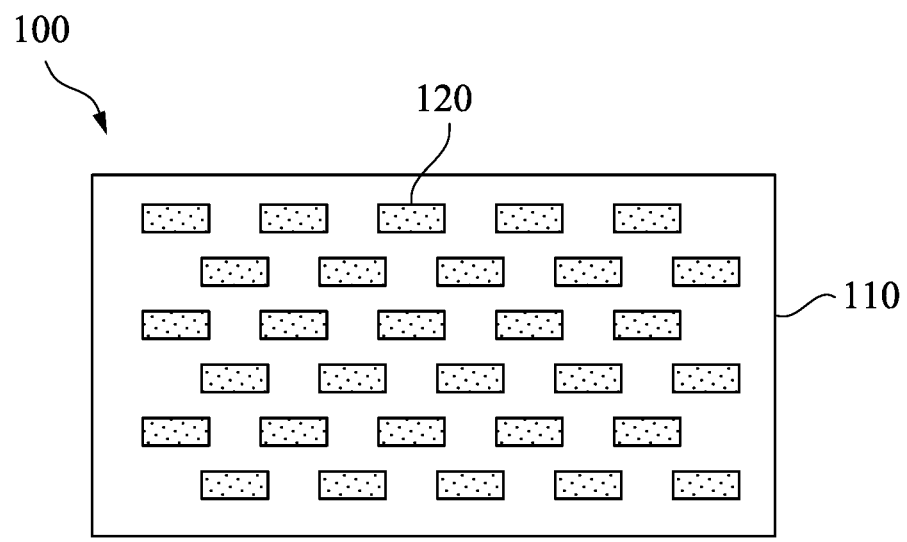
FIG. 3 is a top view of the stereoscopic conductive fabric in FIG. 1.

Then, a description is provided with reference to FIG. 1 and FIG. 3. FIG. 3 is a top view of the stereoscopic conductive fabric 100 in FIG. 1. FIG. 3 mainly depicts relationships between the conductive structures 120. As shown in FIG. 1, portions of the conductive yarns 122 exposed from the basement yarn layer 110 protrude to serve as the conductive structures 120. Since the interlacing and overlapping portion of the two immediately adjacent conductive structures 120 cannot collect more electric charges on the body skin, the wave crests 126 of each of the conductive yarns 122 do not align with the wave crests 126 of the immediately adjacent conductive yarn 122 so that the conductive structures 120 are waves out of alignment to collect more electric charges on the body skin. In other words, the plurality of conductive structures 120 respectively formed by the two adjacent conductive yarns 122 are out of alignment. The two adjacent conductive yarns 122 may be spaced the warp yarn(s) 114 apart. That is, there is at least one warp yarn 114 between each two immediately adjacent conductive yarns 122.

Figure 4:
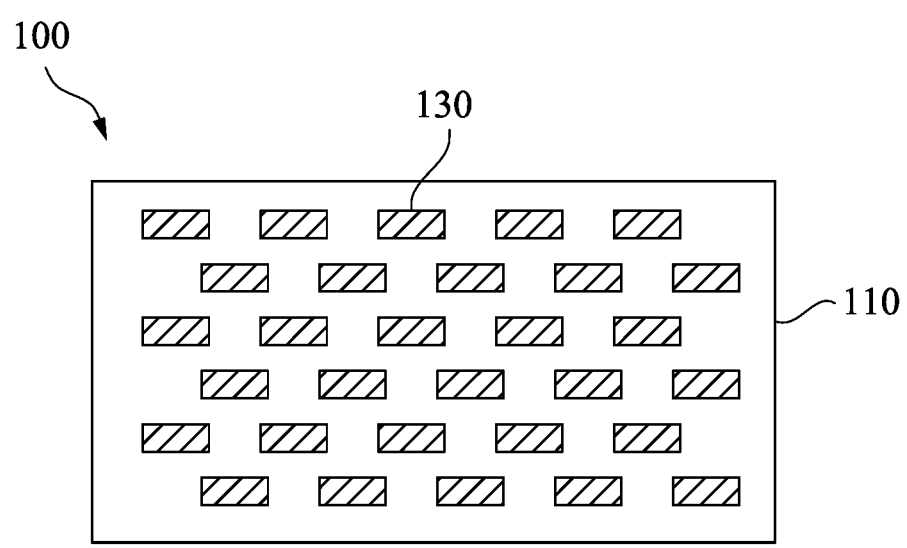
FIG. 4 is a bottom view of the stereoscopic conductive fabric in FIG. 1.

After that, a description is provided with reference to FIG. 1 and FIG. 4. FIG. 4 is a bottom view of the stereoscopic conductive fabric 100 in FIG. 1. FIG. 4 mainly is relationships between the pressing structures 130. As shown in FIG. 1, portions of the support yarns 132 exposed from the basement yarn layer 110 protrude to serve as the pressing structures 130. In order to allow the pressing structures 130 to provide a more uniform support force, the wave troughs 134 of each of the support yarns 132 do not align with the wave troughs 134 of the immediately adjacent support yarn 132 so that the pressing structures 130 in a form of waves out of alignment are formed. The two adjacent support yarns 132 may be spaced the warp yarn(s) 114 apart. That is, there is at least one warp yarn 114 between each two immediately adjacent support yarns 132.

Figure 5:
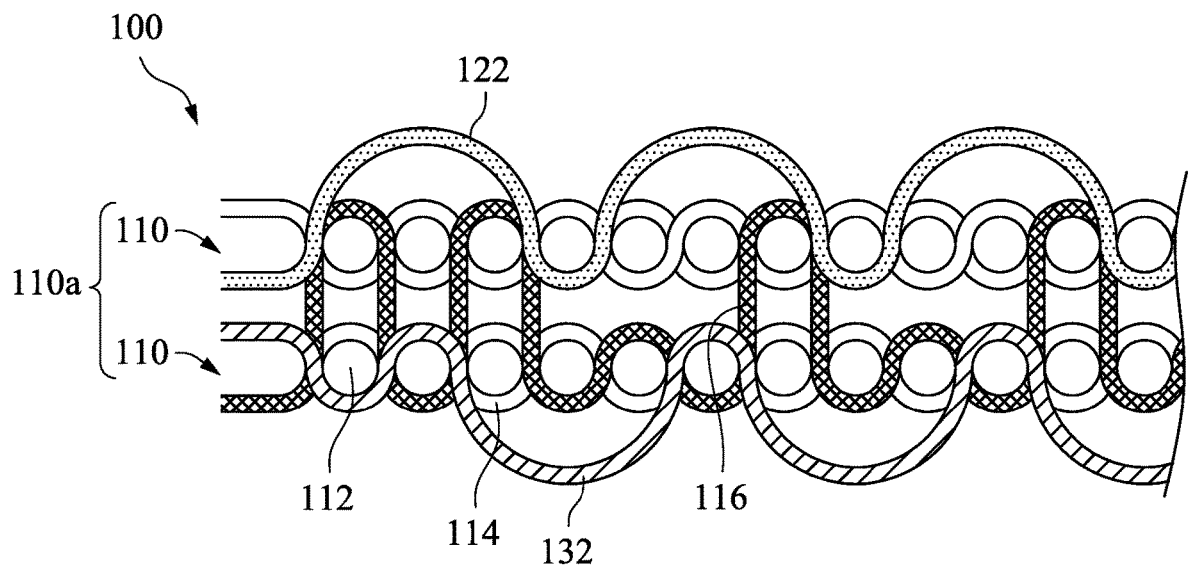
FIG. 5 and FIG. 6 respectively are side schematic diagrams of stereoscopic conductive fabrics according to various embodiments of this invention.
Figure 6:
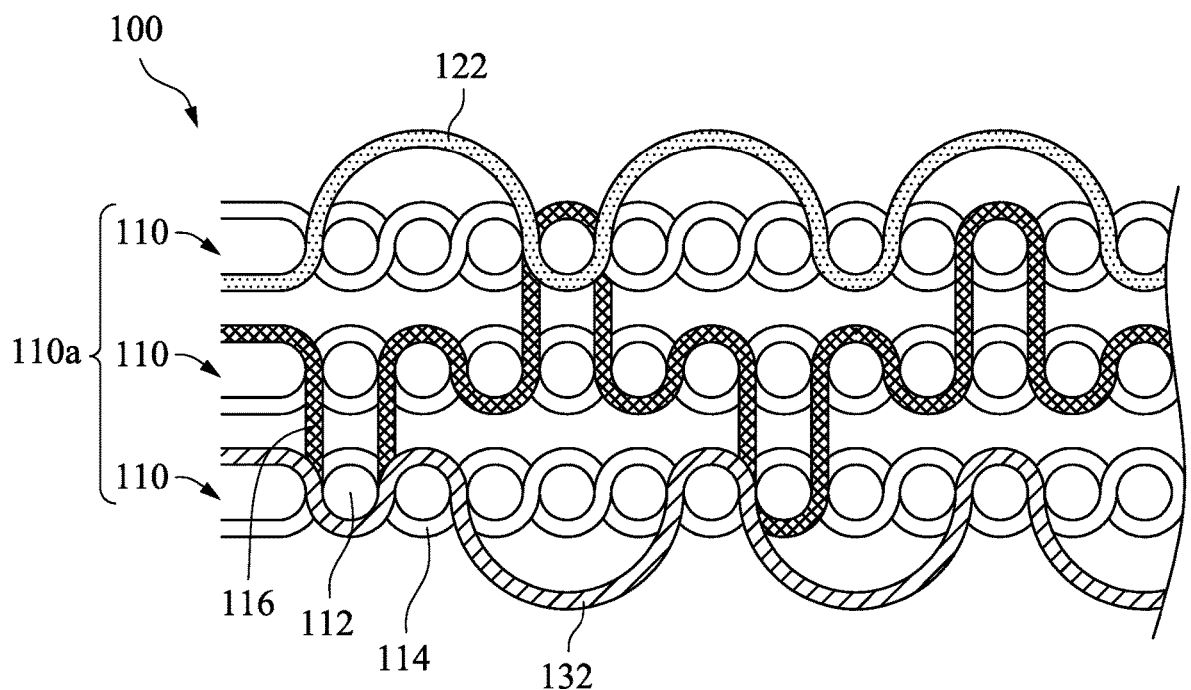

Then, a description is provided with reference to FIG. 5. FIG. 5 is a side schematic diagram of a stereoscopic conductive fabric according to another embodiment of this invention. A difference between the present embodiment and the previous embodiment is that a basement yarn layer 110a of the stereoscopic conductive fabric 100 is in a multi-layered structure, for example, a double-layered structure, which is formed by stacking two layers of the basement yarn layers 110 show in FIG. 1. The basement yarn layer 110a further comprises a connecting yarn 116 to connect a plurality of layers of the basement yarn layers 110 through the connecting yarn 116. The conductive yarns 122 and the support yarns 132 are respectively interwoven with the two outmost basement yarn layers 110. Of course, in other embodiments, the basement yarn layer 110a in the multi-layered structure may comprise more than two basement yarn layers 110. As shown in FIG. 6, the basement yarn layer 110a has three basement yarn layers 110 and the three basement yarn layers 110 are connected by the connecting yarn 116. A number of layers of the basement yarn layer 110a described in the previous embodiments is not intended to limit the present invention, and those of ordinary skill in the art may select suitable number of layers depending on different design requirements.

The above-mentioned stereoscopic conductive fabric 100 can be applied to a module for detecting electrical signals from body skin to resolve the problem that the prior art electrode patch is difficult to operate in the environment having an excessively high or low humidity. The module for detecting electrical signals from body skin applying the stereoscopic conductive fabric 100 has the functions of moisture retention and water retention, such that excess moisture is stored when the humidity of the external environment is excessively high and the moisture stored is released when the humidity of the external environment is excessively low. As a result, the module for detecting electrical signals from body skin can operate normally in environments with humidity difference. In addition, the module for detecting electrical signals from body skin is detachably fastened on the fabric so that a wearer can attach the module for detecting electrical signals from body skin onto different fabrics thereby increasing the flexibility of using the module for detecting electrical signals from body skin. A detailed description is provided with reference to embodiments as follows.

Figure 7A:
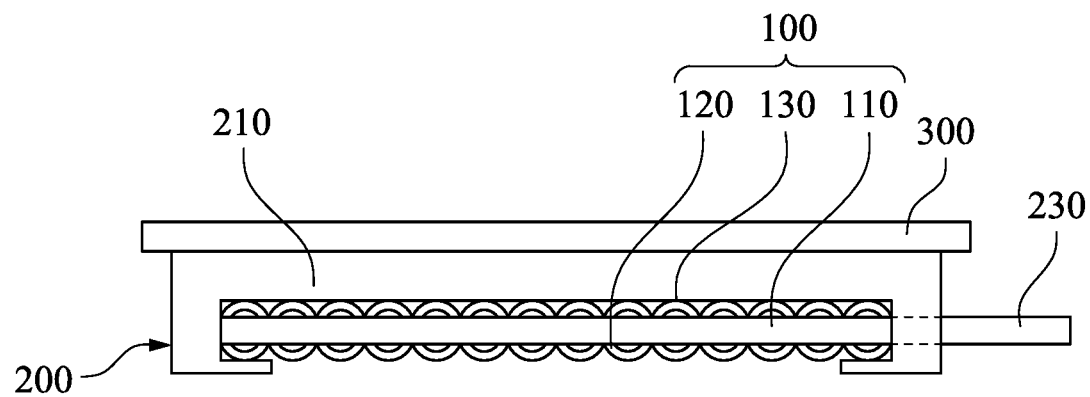
FIG. 7A and FIG. 7B respectively are a cross-sectional schematic diagram and a front schematic diagram of a module for detecting electrical signals from body skin according to a first embodiment of this invention.
Figure 7B:
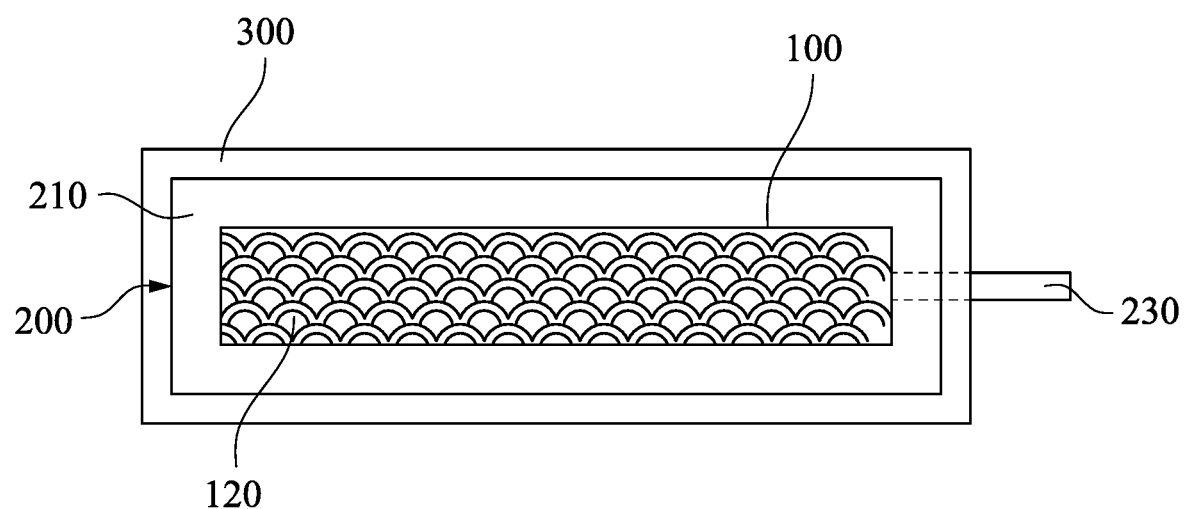

A description is provided with reference to and FIG. 7B. FIG. 7A and FIG. 7B respectively are a cross-sectional schematic diagram and a front schematic diagram of a module for detecting electrical signals from body skin according to a first embodiment of this invention. A module for detecting electrical signals from body skin 200 (hereinafter referred to as "the detecting module 200") comprises a hydrophobic carrier 210, the stereoscopic conductive fabric 100 disposed on the hydrophobic carrier 210, and a conducting device 230 electrically connected to the stereoscopic conductive fabric 100. The detecting module 200 is detachably fastened on a fabric 300, and touches the fabric 300 with the hydrophobic carrier 210 and touches body skin with the stereoscopic conductive fabric 100 in use.

The stereoscopic conductive fabric 100 comprises the basement yarn layers 110 and the plurality of conductive structures 120 and the plurality of pressing structures 130 respectively disposed on the two opposite surfaces of the basement yarn layer 110. The stereoscopic conductive fabric 100 is affixed to the hydrophobic carrier 210 by facing the pressing structures 130 to the hydrophobic carrier 210. In other words, the stereoscopic conductive fabric 100 touches the hydrophobic carrier 210 with the pressing structures 130, and touches the body skin with the conductive structures 120 so as to detect the physiological state, such as an electrocardiogram, an eye on gambling signal, an electroencephalogram, or an electromyogram. In greater detail, the conductive structures 120 can convert collected electric charges on the body skin to electrical signals correspondingly, and the electrical signals thus generated by the conductive structures 120 are transmitted by the conducting device 230.

The water retention capacity of the basement yarn layer 110 is more than or equal to those of the conductive structures 120 and the pressing structures 130. The material of the basement yarn layer 110 may be a moisture retention fiber, such as cotton, rayon, or wool, etc. In some embodiments, the basement yarn layer 110 is, for example, constituted by hollow fibers having a high moisture retention capacity so as to achieve an even higher water retention capacity by utilizing hollow structures in the fibers.

The conductive structure 120 may be a stereoscopic conductive yarn structure. For example, the conductive structure 120 is constituted by a conductive yarn. The conductive yarns are interwoven with the basement yarn layer 110 in a skip manner to form the conductive structures 120 protruding from the surface of the basement yarn layer 110.

As mentioned previously, in order to resolve the problem that electrodes are short circuited because of sweat when a person wears the detecting module 200, a conductive yarn having a water transmitting property is preferably adopted to form the conductive structure 120. The conductive structures 120 are thus able to absorb sweat or moisture on the body skin when touching the body skin, and transmit the absorbed sweat or moisture into the basement yarn layer 110 that contacts the conductive structures 120 by way of the capillary effect. Since the hydrophobic carrier 210 is disposed on an outer side of the basement yarn layer 110, that is, a side away from the body skin, the hydrophobic carrier 210 can be used for isolating moisture from an external environment so as to avoid that moisture directly dissipates from the outer side of the basement yarn layer 110. In this manner, moisture is retained in the basement yarn layer 110 having a better water retention capacity. Not only can this mechanism avoid that too much sweat accumulates on a surface of the stereoscopic conductive fabric 100, which in turn causes the short circuit of electrodes, but excess water can also be stored in the basement yarn layer 110. The water stored in the basement yarn layer 110 can be released to wet the conductive structures 120 when the outside humidity is excessively low to allow the conductive structures 120 to operate normally. Hence, a surface area of the stereoscopic conductive fabric 100 is preferably smaller than a surface area of the hydrophobic carrier 210 to block the water in the basement yarn layer 110 within the hydrophobic carrier 210.

Since the detecting module 200 is detachably fastened on a surface of the fabric 300, the stereoscopic conductive fabric 100 has the pressing structures 130 to ensure a stable contact between the stereoscopic conductive fabric 100 and the body skin. In greater detail, the pressing structures 130 are located between basement yarn layer 110 and the hydrophobic carrier 210. A material of the pressing structure 130 is a support yarn with a higher level of stiffness. Stiffness of the support yarn is at least greater than stiffness of basement yarn layer 110, and the support yarns are interwoven with the basement yarn layer 110 in the skip manner to form the pressing structures 130 protruding from the another surface of the basement yarn layer 110.

The pressing structures 130 are disposed between the basement yarn layer 110 and the hydrophobic carrier 210 to provide sufficient elastic forces so as to press the conductive structures 120 to touch the body skin. In addition, since the pressing structures 130 are hidden in the detecting module 200, that is, the stereoscopic conductive fabric 100 is embedded in the hydrophobic carrier 210, the appearance of the detecting module 200 is not affected, and the stereoscopic conductive fabric 100 can touch the body skin with a substantially flat surface. In other words, the stereoscopic conductive fabric 100 does not protrude towards the body skin, thus reducing the discomfort of a user when wearing the detecting module 200.

The conducting device 230 is configured to transmit the electrical signals generated by the stereoscopic conductive fabric 100 to, for example, an external processor or the like to perform a subsequent function, such as displaying, recording, or monitoring, etc. A suitable type of the conducting device 230 may be selected depending on the connection method between the detecting module 200 and fabric. For example, the conducting device 230 according to the present embodiment is a conductive band (hereinafter referred to as "the conductive band 230"). One end of the conductive band 230 is fixed between the stereoscopic conductive fabric 100 and the hydrophobic carrier 210 and contacts the conductive structures 120 to receive and transmit the electrical signals generated by the conductive structures 120. Another end of the conductive band 230 is exposed from the detecting module 200 and is configured to connect to the external processor. A material of the conductive band 230 may be metal (such as silver or copper) or a material comprising conductive fibers (such as rubber comprising conductive fibers).

In summary, when a wearer wears fabric disposed with the detecting module 200, especially when the wearer exercises, sweat flowing out through the body skin can be guided to the basement yarn layer 110 by the conductive structures 120 and stored in the basement yarn layer 110 so as to avoid the short-circuit problem of the stereoscopic conductive fabric 100 because of sweat. The hydrophobic carrier 210 has the effect of isolating water to avoid direct evaporation of the water, and the water stored in the basement yarn layer 110 can be released to wet the conductive structures 120 when the external environment is excessively dry. The conductive structures 120 can thus sense normally. The conductive structures 120 of the stereoscopic conductive fabric 100 may touch against the body skin by the pressing structures 130. In addition, since the stereoscopic conductive fabric 100 is disposed within the hydrophobic carrier 210, the appearance of the detecting module 200 is flat without causing discomfort of the wearer because the detecting module 200 does not protrude towards the body skin.

Figure 8A:
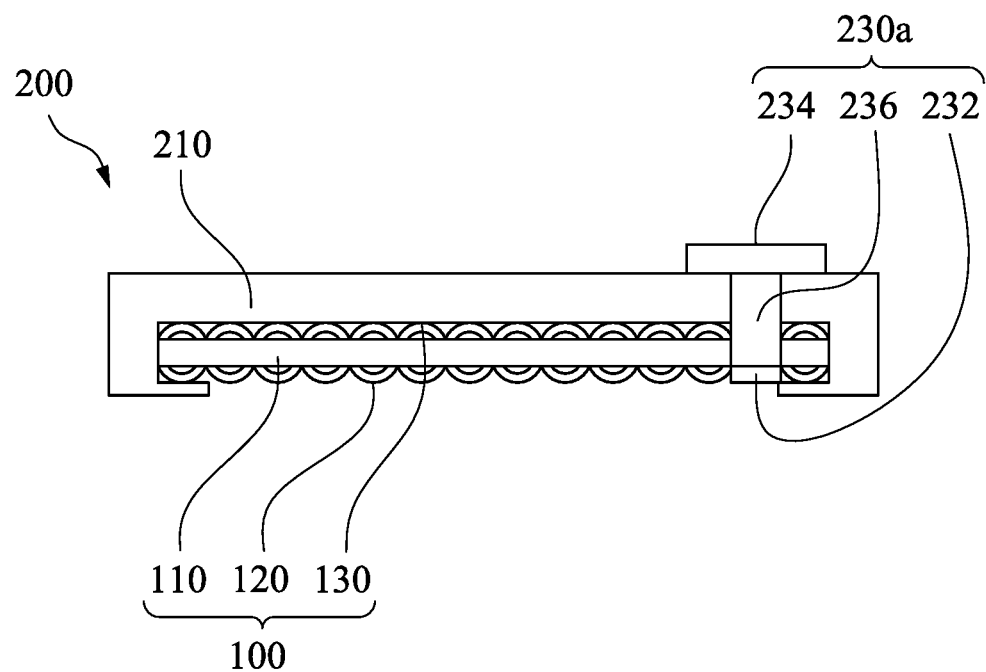
FIG. 8A and FIG. 8B respectively are a cross-sectional schematic diagram and a front schematic diagram of a module for detecting electrical signals from body skin according to a second embodiment of this invention.
Figure 8B:
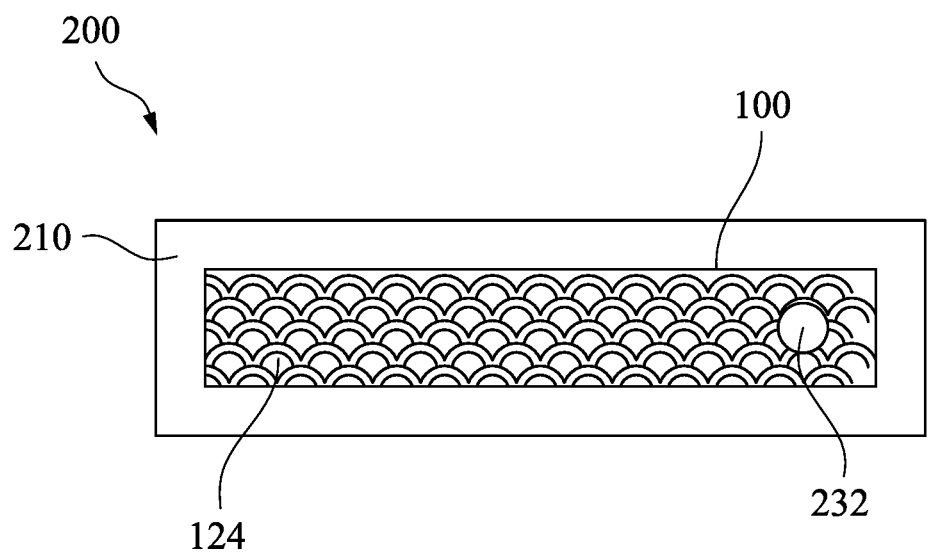

Then, a description is provided with reference to FIG. 8A and FIG. 8B. FIG. 8A and FIG. 8B respectively are a cross-sectional schematic diagram and a front schematic diagram of a module for detecting electrical signals from body skin according to a second embodiment of this invention. A difference between the present embodiment and the first embodiment is that a conducting device 230a according to the present embodiment comprises a first contact pad 232 connecting to the conductive structures 120, a second contact pad 234 disposed on the hydrophobic carrier 210, and a conductive pillar 236 connecting the first contact pad 232 and the second contact pad 234. Electric charges on the body skin collected by the conductive structures 120 are converted to the electrical signals and is then transmitted to an outside via the first contact pad 232, the conductive pillar 236, and the second contact pad 234 in sequence.

The first contact pad 232 may be embedded in the stereoscopic conductive fabric 100 so that the detecting module 200 touches body skin with a substantially flat surface according to the present embodiment. The second contact pad 234 is exposed from the detecting module 200 to allow the detecting module 200 to be connected to external circuits. Materials of the first contact pad 232, the second contact pad 234, and the conductive pillar 236 may comprise the same metal or different metals.

Figure 9:
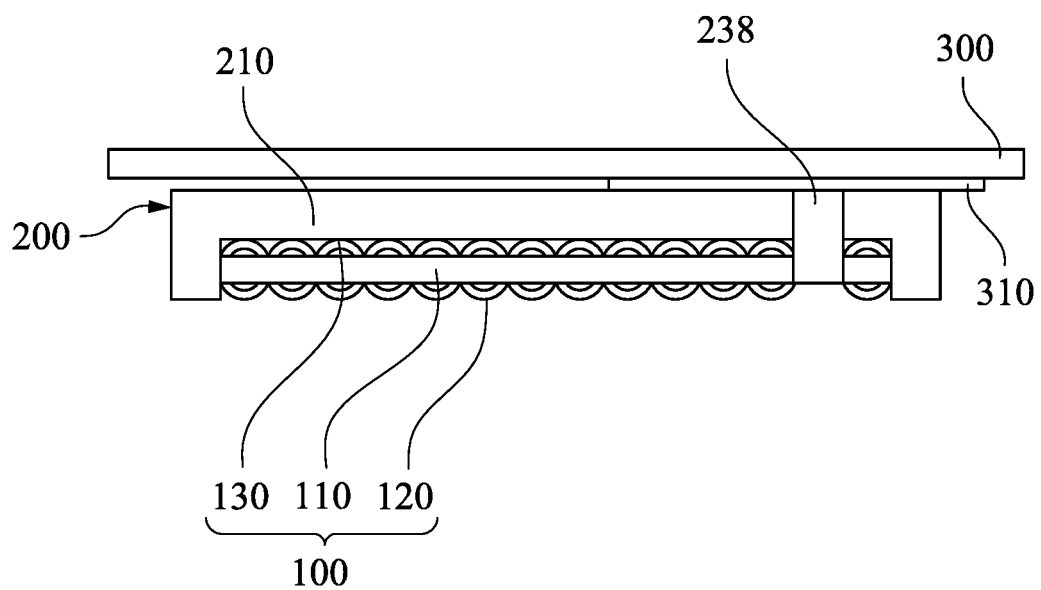
FIG. 9 is a cross-sectional schematic diagram of a module for detecting electrical signals from body skin according to a third embodiment of this invention.

A description is then provided with reference to FIG. 9. FIG. 9 is a cross-sectional schematic diagram of a module for detecting electrical signals from body skin according to a third embodiment of this invention. A difference between the present embodiment and the first embodiment is that a conducting device according to the present embodiment is a magnet 238 disposed in the detecting module 200. The magnet 238 is further connected to the conductive structures 120 and exposed from the hydrophobic carrier 210. The detecting module 200 is connected to a metal electrode 310 disposed on the fabric 300 in advance via the magnet 238 to conduct. The metal electrode 310 may be fixed to the fabric 300 in advance by using a suitable method, such as adhering or engaging. A material of the metal electrode 310 may be selected from materials having iron, cobalt, nickel, or alloy(s) thereof, etc. and being able to be attracted by the magnet 238.

By utilizing the magnetic attraction force between the metal electrode 310 and the magnet 238, the metal electrode 310 can be attached to a surface of the stereoscopic conductive fabric 100 to allow the electrical signals generated by the conductive structures 120 to be transmitted to the metal electrode 310 that contacts the magnet 238 via the magnet 238 and then transmitted to a processor via the metal electrode 310.

Figure 10:
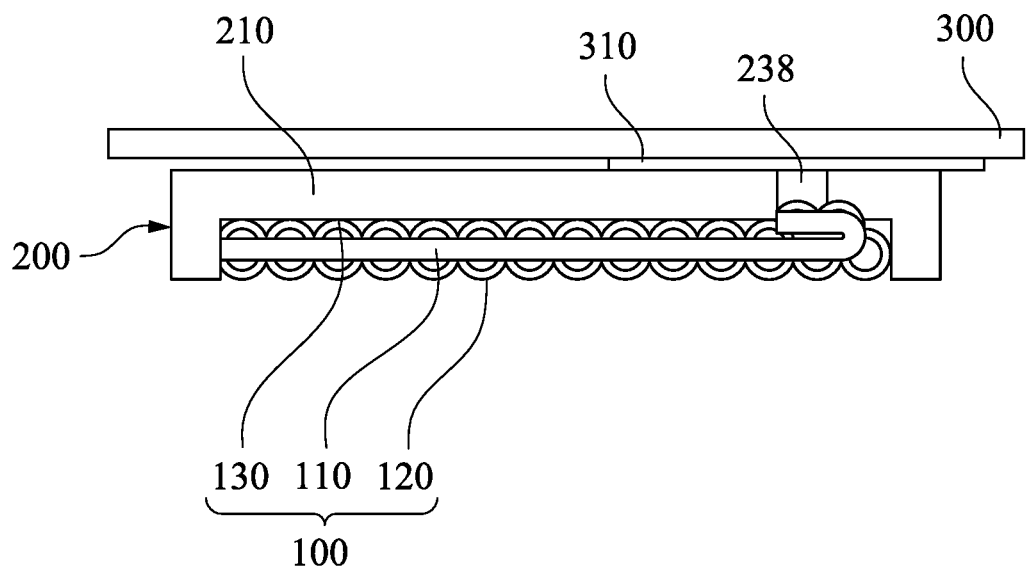
FIG. 10 is a cross-sectional schematic diagram of a module for detecting electrical signals from body skin according to a fourth embodiment of this invention.

FIG. 10 is a cross-sectional schematic diagram of a module for detecting electrical signals from body skin according to a fourth embodiment of this invention. Or, as shown in FIG. 10, the magnet 238 in the detecting module 200 is disposed between the stereoscopic conductive fabric 100 and the hydrophobic carrier 210, and one end of the magnet 238 is exposed from the hydrophobic carrier 210 and can be magnetically attracted to the metal electrode 310 disposed on the fabric 300 in advance. The stereoscopic conductive fabric 100 can be reflexed so that the conductive structures 120 can be directly connect to the magnet 238. The electrical signals generated by the conductive structures 120 can thus be transmitted to the magnet 238 that contacts the conductive structures 120 and then transmitted to the metal electrode 310 that contacts the magnet 238 via the magnet 238.

Figure 11A:
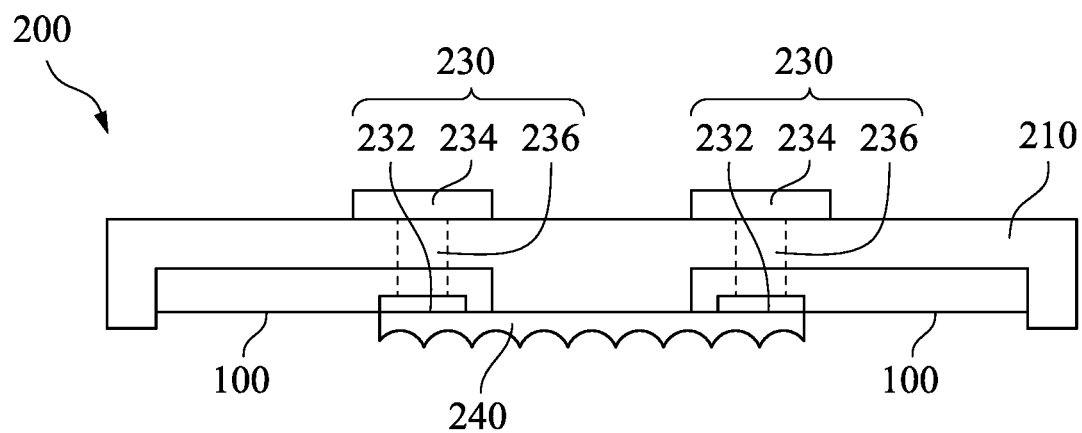
FIG. 11A and FIG. 11B respectively are a cross-sectional schematic diagram and a front schematic diagram of a module for detecting electrical signals from body skin according to a fifth embodiment of this invention.
Figure 11B:
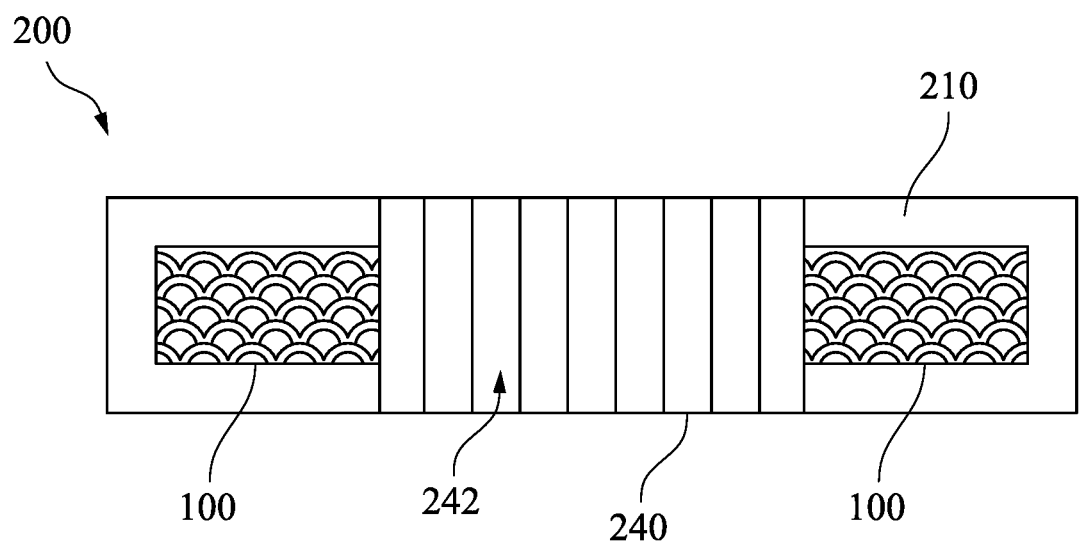

Then, a description is provided with reference to FIG. 11A and FIG. 11B. FIG. 11A and FIG. 11B respectively are a cross-sectional schematic diagram and a front schematic diagram of a module for detecting electrical signals from body skin according to a fifth embodiment of this invention. The detecting module 200 comprises the hydrophobic carrier 210, the two stereoscopic conductive fabrics 100 disposed on the hydrophobic carrier 210, the two conducting devices 230, and a waterproof isolator 240 disposed between the stereoscopic conductive fabric 100.

The two stereoscopic conductive fabrics 100 are spaced a specific distance apart and do not contact each other directly. The waterproof isolator 240 is disposed between the two stereoscopic conductive fabrics 100 to avoid that the two stereoscopic conductive fabrics 100 are directly conducted because of moisture, such as sweat, on the body skin.

The waterproof isolator 240 is disposed on the hydrophobic carrier 210 and located between the two stereoscopic conductive fabrics 100. The waterproof isolator 240 has a plurality of grooves 242 parallel to one another. An extension direction of the grooves 242 is not parallel to a connection line between the two stereoscopic conductive fabrics 100 to provide a better effect on isolating water drops so as to avoid that the water drops move forwards along the grooves 242 to conduct the two stereoscopic conductive fabrics 100. For example, the grooves 242 according to the present embodiment are perpendicular to the connection line between the two stereoscopic conductive fabrics 100. In addition, a width of the waterproof isolator 240 is preferably greater than a width of the stereoscopic conductive fabrics 100 to ensure the waterproof effect of the waterproof isolator 240.

Since materials and structures of the hydrophobic carrier 210 and the stereoscopic conductive fabrics 100 are the same as those described in the previous embodiments, a description in this regard is not provided. Additionally, although the first contact pad 232, the second contact pad 234, and the conductive pillar 236 together serve as the conducting device 230 according to the present embodiment, however, in practice the conducting device 230 may be the conductive band shown in FIG. 7A or the magnet shown in FIG. 9, and the present invention is not limited in this regard.

The detecting module 200 may further cooperate with a detecting device and the two stereoscopic conductive fabrics 100 are respectively used as a positive electrode and a negative electrode of the detecting device, and signals detected by the detecting device is transmitted to the outside by the conducting device 230.

Figure 12A:
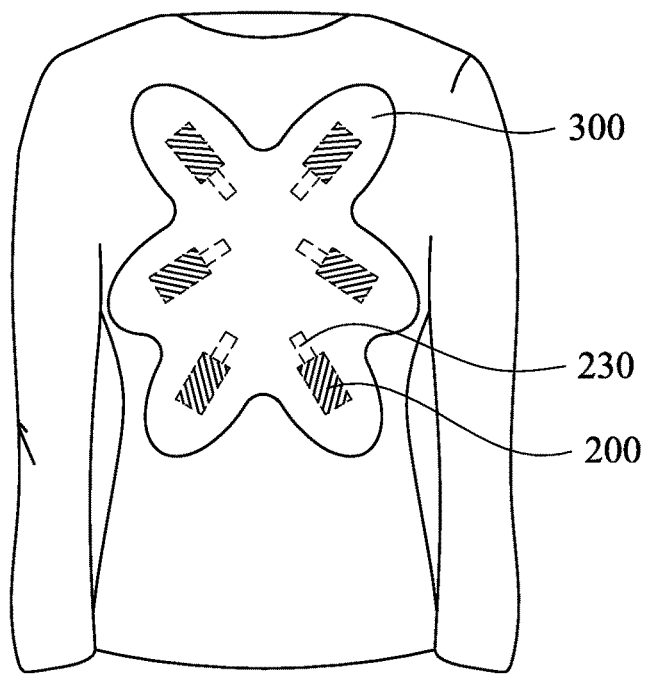
FIG. 12A and FIG. 12B respectively are schematic diagrams of a module for detecting electrical signals from body skin according to different embodiments of this invention in use.
Figure 12B:
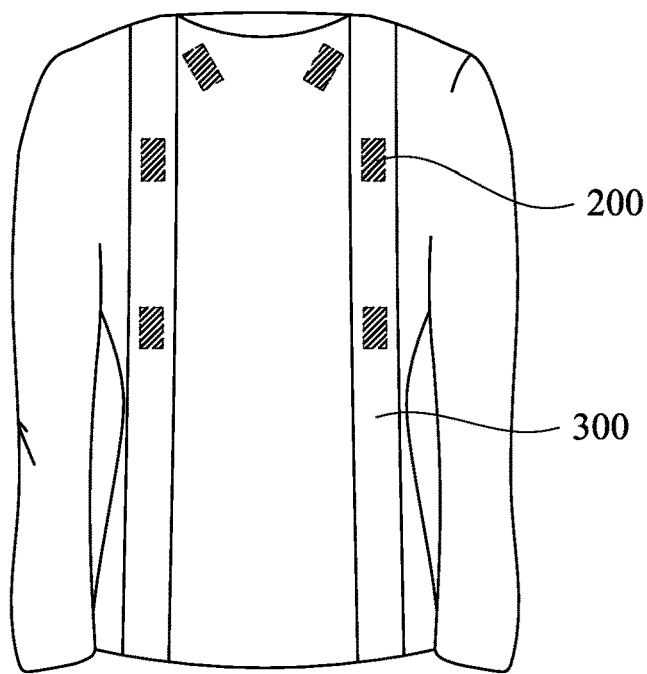

A description is provided with reference to FIG. 12A and FIG. 12B. The detecting module 200 may be applied to providing real-time physiological information of the wearer, such as an electrocardiogram, an eye on gambling signal, an electroencephalogram, or an electromyogram, etc. The detecting module 200 may be detachably fastened on the fabric 300 for touching the body skin of the wear so as to perform detection.

The fabric 300 may be, for example, apparel, such as clothing, pants, leg sleeves, cuffs, gloves, socks, caps, masks, eye masks, hats, scarves, vests, suspenders, etc., or protective garments, such as knee pads, waist supports, shoulder pads, maternity belts, etc. A number of the modules for detecting electrical signals from body skin 200 disposed on the fabric 300 and a position at which the detecting module 200 is disposed on the fabric 300 may be changed depending on various requirements. For example, in the embodiment shown in FIG. 12A, the plurality of detecting modules 200 are disposed on the fabric 300, such as a shirt, in which the detecting modules 200 having the conducting devices 230 are arranged in a radius manner. In the embodiment of FIG. 12B, the plurality of detecting modules 200 are disposed on the fabric 300, such as a shirt, in which the detecting modules 200 are arranged in a linear manner.

Figure 13:
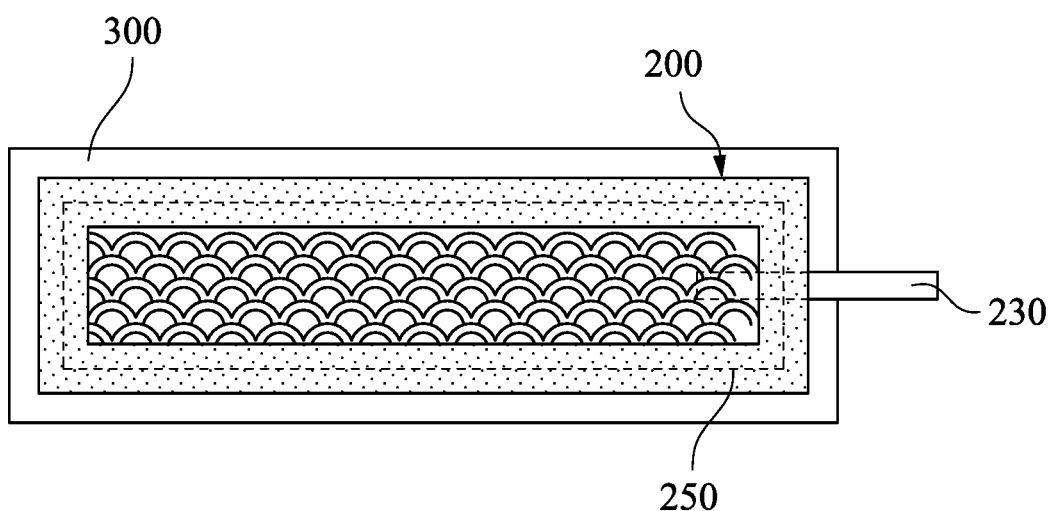
FIG. 13 is a cross-sectional schematic diagram of a module for detecting electrical signals from body skin according to a sixth embodiment of this invention.

FIG. 13 is a front schematic diagram of a module for detecting electrical signals from body skin according to a sixth embodiment of this invention. In order to detachably fasten the detecting module 200 on the fabric 300, the detecting module 200 further comprises a connection element 250 configured to temporarily or detachably fasten the detecting module 200 on the fabric 300.

For example, the connection element 250 may be adhesive so that the detecting module 200 is detachably fastened on the fabric 300 through adhering. The connection element 250 may also be sewing thread, and the detecting module 200 is detachably fastened on the fabric 300 through sewing. Or, the connection element 250 may be a fastener. The fastener is fixed to the detecting module 200, and another fastener is disposed on the fabric 300 corresponding to the fastener so that the detecting module 200 is detachably fastened on the fabric 300 through engaging. The connection element 250 may also be Velcro or terry fabric. Velcro or an adhesion block is disposed on the fabric 300 corresponding to the Velcro or terry fabric so that the detecting module 200 can be adhered to the fabric 300. In some embodiments, the connection element 250 can even be integrated with the conducting device 230. For example, a magnetic material, such as a magnet or a colloid containing magnetic powder, is utilized to serve as the conducting device 230 and the connection element 250 at the same time. Both objectives of signal transmission and fixing the module for detecting electrical signals from body skin can thus be achieved by magnetically attracting the magnetic material to a metal electrode on the fabric 300.

In summary, the present invention provides a stereoscopic conductive fabric in which yarns made of different materials are interwoven to obtain the conductive structures and the pressing structures protruding from the two opposite surfaces of the basement yarn layer. The conductive structures are used for touching the body skin to receive the electric charges generated by the body skin. The pressing structures are used for providing a sufficient supportive elastic force to allow the conductive structures to touch against the body skin. The stereoscopic conductive fabric can further have the effect of water retention by selecting the suitable yarn materials, thus avoiding the short circuit between conductive structures due to sweat on the body skin. The module for detecting electrical signals from body skin applying the stereoscopic conductive fabric is able to store excess moisture when the humidity of the external environment is excessively high and release the moisture stored when the humidity of the external environment is excessively low. As a result, the module for detecting electrical signals from body skin can operate normally in environments with humidity difference. In addition, the module for detecting electrical signals from body skin is detachably fastened on the fabric so that a wearer can attach the module for detecting electrical signals from body skin onto different fabrics to increase the flexibility of using the module for detecting electrical signals from body skin and facilitate the cleaning of the fabric.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A module for detecting electrical signals from body skin, the module being detachably fastened on a fabric for touching body skin, the module comprising:
　a hydrophobic carrier;
　at least one stereoscopic conductive fabric disposed on the hydrophobic carrier, the stereoscopic conductive fabric comprising a basement yarn layer and a plurality of conductive structures and a plurality of pressing structures respectively disposed on two opposite surfaces of the basement yarn layer, the stereoscopic conductive fabric touching the hydrophobic carrier with the pressing structures and touching the body skin with the conductive structures, wherein the basement yarn layer comprises:
　　a plurality of course yarns arranged warpwise and parallel to each other; and
　　a plurality of warp yarns arranged coursewise and parallel to each other, the warp yarns being interwoven with the course yarns to form the basement yarn layer,
　wherein the stereoscopic conductive fabric comprises:
　　a conductive yarn arranged coursewise and interwoven with the course yarns in a skip manner to form a plurality of conductive structures protruding from a surface of the basement yarn layer; and
　　a support yarn arranged coursewise and interwoven with the course yarns in a skip manner to form a plurality of pressing structures protruding from another surface of the basement yarn layer; and
　a conducting device disposed on the hydrophobic carrier and electrically connected to the conductive structures to transmit electrical signals generated by the conductive structure.

2. The module for detecting electrical signals from body skin of claim 1, wherein a number of the stereoscopic conductive fabrics is two, the module for detecting electrical signals from body skin further comprises:
　a waterproof isolator disposed between the two stereoscopic conductive fabrics and touching the body skin.

3. The module for detecting electrical signals from body skin of claim 2, wherein the waterproof isolator is connected to the hydrophobic carrier and comprises a plurality of grooves parallel to one another.

4. The module for detecting electrical signals from body skin of claim 1, wherein the conducting device comprises a first contact pad connecting to the conductive structures, a second contact pad disposed on the hydrophobic carrier, and a conductive pillar connecting the first contact pad and the second contact pad.

5. The module for detecting electrical signals from body skin of claim 1, wherein the conducting device comprises a conductive band, one end of the conductive band is connected to the conductive structures, and another end of the conductive band is exposed from the module for detecting electrical signals from body skin.

6. The module for detecting electrical signals from body skin of claim 1, wherein the conducting device comprises a magnet, and the magnet is connected to the conductive structures and exposed from the module for detecting electrical signals from body skin.

7. The module for detecting electrical signals from body skin of claim 1, wherein a surface area of the stereoscopic conductive fabric is smaller than a surface area of the hydrophobic carrier, and the stereoscopic conductive fabric is embedded in the hydrophobic carrier.

8. The module for detecting electrical signals from body skin of claim 1, wherein the stereoscopic conductive fabric comprises a conductive yarn interwoven with the basement yarn layer in a skip manner to form the conductive structures protruding from a surface of the base yarn layer.

9. The module for detecting electrical signals from body skin of claim 8, wherein the conductive yarn comprises a plurality of wave crests protruding from the basement yarn layer and a plurality of wave troughs hidden in the basement yarn layer, the wave crests of the conductive yarn are not aligned with wave crests of another conductive yarn adjacent to the conductive yarn, and the wave troughs of the conductive yarn are not aligned with wave troughs of the another conductive yarn adjacent to the conductive yarn.

10. The module for detecting electrical signals from body skin of claim 8, wherein the conductive yarn comprises yarns made of different conductive materials or yarns with different electric conductivities.

11. The module for detecting electrical signals from body skin of claim 1, wherein the stereoscopic conductive fabric comprises a support yarn interwoven with the basement yarn layer in a skip manner to form support structures protruding from another surface of the base yarn layer.

12. The module for detecting electrical signals from body skin of claim 11, wherein the support yarn comprises wave troughs protruding from the basement yarn layer and wave crests hidden in the basement yarn layer, the wave crests of the support yarn are not aligned with wave crests of another support yarn adjacent to the support yarn, and the wave troughs of the support yarn are not aligned with wave troughs of the another support yarn adjacent to the support yarn.

13. The module for detecting electrical signals from body skin of claim 1, further comprising a connection element disposed on the hydrophobic carrier and detachably fastened on the stereoscopic conductive fabric.

14. The module for detecting electrical signals from body skin of claim 1, wherein a water absorption property of the basement yarn layer is better than that of the conductive yarn and the support yarn.

15. The module for detecting electrical signals from body skin of claim 1, wherein a stiffness of the support yarn is greater than that of the basement yarn layer and the conductive yarn.

* * * * *